US008546769B2

(12) United States Patent
Uno

(10) Patent No.: US 8,546,769 B2
(45) Date of Patent: Oct. 1, 2013

(54) CHARGED PARTICLE BEAM IRRADIATION APPARATUS, CHARGED PARTICLE BEAM IRRADIATING METHOD, AND METHOD OF ATTACHING AND DETACHING TRANSPORT LINE

(75) Inventor: Kouichi Uno, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 60 days.

(21) Appl. No.: 13/293,171

(22) Filed: Nov. 10, 2011

(65) Prior Publication Data

US 2012/0119106 A1  May 17, 2012

(30) Foreign Application Priority Data

Nov. 11, 2010  (JP) .................... P2010-252644

(51) Int. Cl.
*H01J 3/26* (2006.01)
(52) U.S. Cl.
USPC .................................................. 250/396 ML
(58) Field of Classification Search
USPC ........................................ 250/492.1, 396 ML
See application file for complete search history.

(56) References Cited

U.S. PATENT DOCUMENTS

| | | | | |
|---|---|---|---|---|
| 4,870,287 A | * | 9/1989 | Cole et al. | 250/398 |
| 5,260,581 A | * | 11/1993 | Lesyna et al. | 250/398 |
| 5,349,198 A | * | 9/1994 | Takanaka | 250/396 ML |
| 5,847,401 A | * | 12/1998 | McKeown et al. | 250/396 ML |
| 6,770,888 B1 | * | 8/2004 | Benveniste et al. | 250/396 ML |
| 7,173,264 B2 | * | 2/2007 | Moriyama et al. | 250/398 |
| 7,432,516 B2 | * | 10/2008 | Peggs et al. | 250/492.1 |
| 8,063,381 B2 | * | 11/2011 | Tsoupas et al. | 250/396 ML |

FOREIGN PATENT DOCUMENTS

| | | |
|---|---|---|
| JP | 6-214100 | 8/1994 |
| JP | 11-501232 | 2/1999 |
| JP | 2000-75100 | 3/2000 |

OTHER PUBLICATIONS

European Search Report application No. 11008906.7 Feb. 21, 2012.

\* cited by examiner

*Primary Examiner* — David A Vanore
*Assistant Examiner* — Wyatt Stoffa
(74) *Attorney, Agent, or Firm* — Squire Sanders (US) LLP

(57) ABSTRACT

A charged particle beam irradiation apparatus includes an accelerator that accelerates the charged particle beam; a first transport line that transports the charged particle beam which is delivered from the accelerator; a plurality of second transport lines that may be provided for each of plurality of irradiation chambers and further transports the charged particle beam to be transported by the first transport line to the respective irradiation chambers; and a line switching unit that may be provided between the first transport line and the second transport lines, wherein the plurality of irradiation chambers may be radially disposed around the line switching unit, the line switching unit has an electromagnet that induces the charged particle beam, and a rotating mechanism that rotates the electromagnet, and the second transport lines of the induction place may be switched by rotating the electromagnet.

3 Claims, 8 Drawing Sheets

CHARGED PARTICLE BEAM IRRADIATION APPARATUS, CHARGED PARTICLE BEAM IRRADIATING METHOD, AND METHOD OF ATTACHING AND DETACHING TRANSPORT LINE

RELATED APPLICATION

Priority is claimed to Japanese Patent Application No. 2010-252644, filed Nov. 11, 2010, the entire content of which is incorporated herein by reference.

BACKGROUND

1. Technical Field

Certain embodiments of the present invention relate to a charged particle beam irradiation apparatus, a charged particle beam irradiating method, and a method of attaching and detaching a transport line thereof.

2. Description of the Related Art

In the related art, as a technique of such a field, charged particle beam irradiation apparatuses described in related art are known as described below. In the related art, a plurality of irradiation chambers is disposed in parallel, whereby it is possible to supply a proton beam from one accelerator toward the plurality of irradiation chambers. The apparatus includes a beam transport line that is linearly extended in an arrangement direction of the irradiation chambers, and branching lines that are branched from the beam transport line and are extended to each irradiation chamber, respectively. Moreover, by switching the operating states (On/Off) of electromagnets of each branching point, it is possible to selectively transport the beam to the irradiation chamber to be used. Furthermore, in the related art, a plurality of irradiation chambers is disposed in a fan-like manner, and respective branching lines extended from one branching point of the beam transport line to each irradiation chamber are provided. Moreover, by switching the operating state of the electromagnet of the branching point, it is possible to selectively transport the beam to the irradiation chamber to be used.

SUMMARY

According to an embodiment of the present invention, there is provided a charged particle beam irradiation apparatus that includes a plurality of irradiation chambers, and irradiates irradiation targets in the irradiation chambers with a charged particle beam, the apparatus includes an accelerator that accelerates the charged particle beam; a first transport line that transports the charged particle beam to be delivered from the accelerator; a plurality of second transport lines that are provided for each of plurality of irradiation chambers and further transport the charged particle beam to be transported by the first transport line to the respective irradiation chambers; and line switching means that is provided between the first transport line and the second transport lines, induces the charged particle beam from the first transport line to any of second transport lines, and can selectively switch the second transport line of the induction place, wherein the plurality of irradiation chambers is radially disposed around the line switching means, the line switching means has an electromagnet that induces the charged particle beam, and a rotating mechanism that rotates the electromagnet, and the second transport lines of the induction place are switched by rotating the electromagnet.

DETAILED DESCRIPTION

Figure 1:
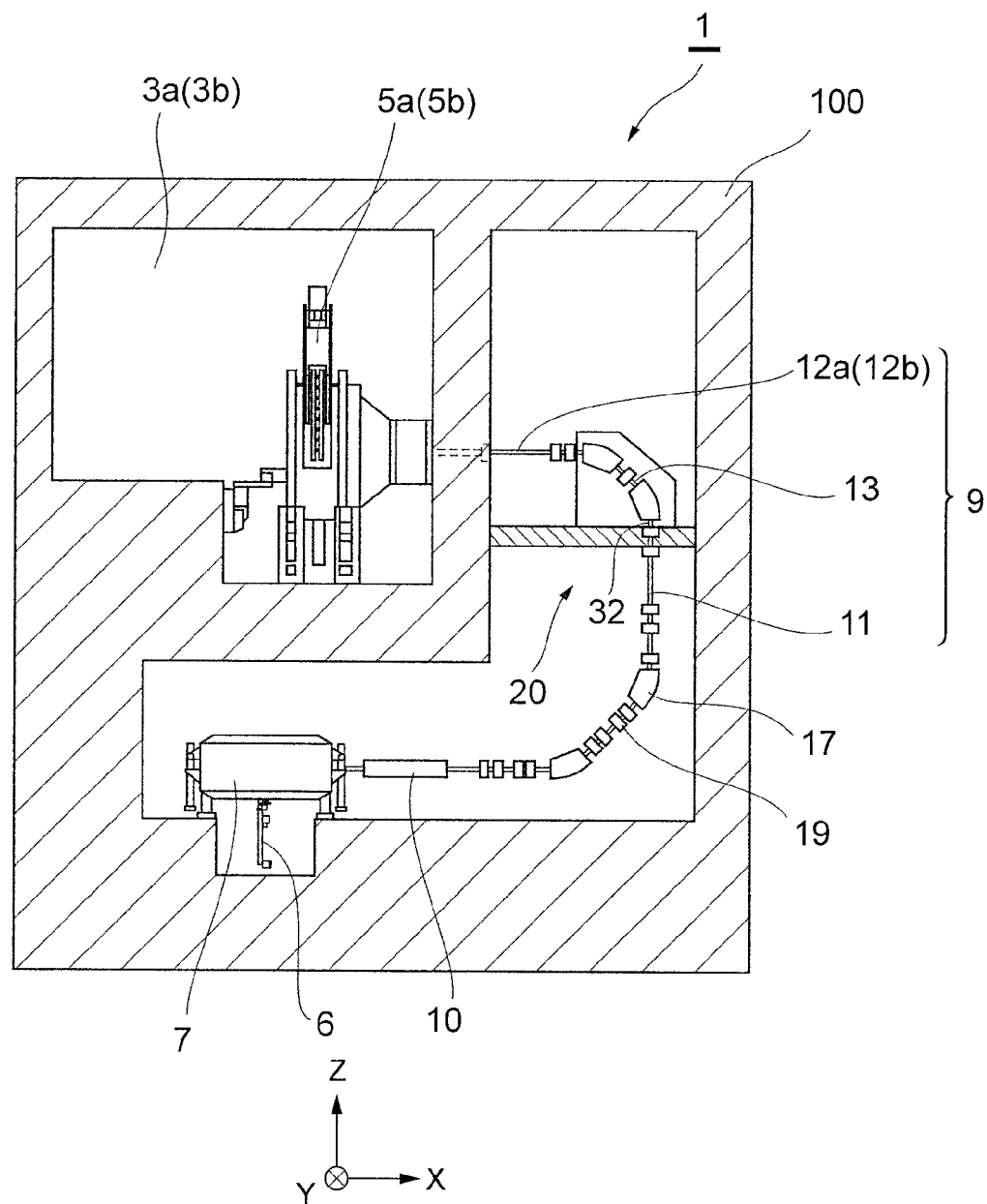
FIG. 1 is a side view that shows a particle beam therapeutic apparatus which is an embodiment of a charged particle beam irradiation apparatus according to the present invention.

However, in the type of apparatus of the related art, as the number of irradiation chambers increases, there is a need to lengthen the beam transport line, and beam shaping electromagnets to be disposed in the beam transport line are increased. Further, also in the type of apparatus of the related art, as the number of irradiation chambers increases, there is an increase in the electromagnets for beam deviation disposed at the branching points. Furthermore, there is a need for a wide site area, depending on a beam deviation angle in the branching point. Furthermore, in the apparatus of the related art, in order to transport the proton beam to a desired irradiation chamber, there is a problem in that the magnetic field of the deviation magnet needs to be accurately controlled.

It is desirable to provide a charged particle beam irradiation apparatus, a charged particle beam irradiating method, and a method of attaching and detaching a transport line thereof that can reduce the number of beam transporting electromagnets, while reducing a site area of an installation place.

In the charged particle beam irradiation apparatus, when sending the charged particle beam to a desired irradiation chamber, the charged particle beam from the first transport line is induced to the second transport line corresponding to the desired irradiation chamber. The induction of the charged particle beam is performed by the electromagnet of the line switching means, and the line switching means switches the second transport line of the induction place by rotating the electromagnet. In this manner, the line switching means adopts the system of rotating the electromagnet as the type of switching the induction place. Thus, it is possible to reduce the required number of electromagnets compared to the type of switching the operating states (On/Off) of the electromagnet. Furthermore, since a plurality of irradiation chambers is radially disposed around the line switching means, unnecessary installation space is reduced, whereby it is possible to reduce the site area of an installation location of the charged particle beam irradiation apparatus.

Furthermore, as a specific configuration, the line switching means may have a tubular connection line that is provided with an electromagnet, mediates the connection between a tubular first transport line and a tubular second transport line, and causes the charged particle beam to pass therethrough; a rotation support portion that rotatably supports the connection line and the electromagnet around a connection portion between one end of the connection line and the first transport line; and a movement connection portion that is provided in the other end of the connection line and is moved in each position capable of being connected to the respective second transport lines along with the rotation of the connection line and the electromagnet.

According to the configuration, by the rotation of the connection line around the connection portion between one end of the connection line and the first transport line, the movement connection portion is moved in each position capable of being connected to the respective second transport lines. Thus, it is possible to move the movement connection portion by the rotation of the connection line and selectively switch the second transport line connecting the movement connection portion, whereby the charged particle beam can be sent to a desired irradiation chamber.

Furthermore, in an upstream end portion of the second transport line, a second transport line opening and closing valve which opens and closes the second transport line may be provided, and the movement connection portion may have a connection line opening and closing valve that opens and closes the connection line, and a tubular expansion and contraction portion that is provided at a downstream side further than the connection line opening and closing valve, and is attached to and detached from the upstream end portion of the second transport line by being expanded and contracted in an advancement direction of the charged particle beam.

According to the configuration, it is possible to perform the connection/disconnection between the second transport line and the connection line, while maintaining the vacuum of a transport path of the charged particle beam.

Furthermore, in the charged particle beam irradiation apparatus of the present invention, a plurality of irradiation chambers and accelerators are provided in different floors of a building, and the first transport line may be extended from the floor provided with the accelerator to the floor provided with the irradiation chamber.

According to the configuration, it is possible to reduce a projection area of the first transport line viewed from the upper part, whereby it is possible to reduce the installation area as a whole of the charged particle beam irradiation apparatus. Furthermore, it is also possible to dispose the irradiation chamber and the accelerator so as to vertically overlap each other, whereby the installation area can be further reduced.

According to another embodiment of the present invention, there is provided a charged particle beam irradiating method of irradiating an irradiation target in the irradiation chamber in a plurality of irradiation chambers with a charged particle beam, the method includes a charged particle beam acceleration step of accelerating the charged particle beam by the accelerator; a first transport step of transporting the charged particle beam accelerated at the charged particle beam acceleration step by a first transport line; a second transport step of transporting the charged particle beam to be transported at the first transport step to the irradiation chambers, by any of second transport lines provided for each of a plurality of irradiation chambers; and a line switching step of selectively switching a second transport line of an induction place by line switching means that is provided between the first transport line and the second transport lines and induces the charged particle beam from the first transport line to any of second transport lines, wherein the plurality of irradiation chambers is radially disposed around the line switching means, the line switching means has an electromagnet that induces the charged particle beam, and a rotating mechanism that rotates the electromagnet, and, at the line switching step, the second transport lines of the induction place are switched by rotating the electromagnet.

In the charged particle beam irradiating method, when sending the charged particle beam to a desired irradiation chamber, the charged particle beam from the first transport line is induced to the second transport line corresponding to the desired irradiation chamber. The induction of the charged particle beam is performed by the electromagnet of the line switching means, and, at the line switching step, the second transport line of the induction place is switched by rotating the electromagnet. In this manner, at the line switching step, the type of rotating the electromagnet is adopted as the type of switching the induction place by the line switching means. Thus, it is possible to reduce the required number of electromagnets compared to the type of switching the operating states (On/Off) of the electromagnet. Furthermore, since a plurality of irradiation chambers is radially disposed around the line switching means, an unnecessary installation space is reduced, whereby it is possible to reduce a site area of an installation location of the charged particle beam irradiation apparatus.

Furthermore, in the charged particle beam irradiating method, the line switching means may have a tubular connection line that is provided with an electromagnet, mediates the connection between a tubular first transport line and a tubular second transport line, and causes the charged particle beam to pass therethrough; a rotation support portion that rotatably supports the connection line and the electromagnet around a connection portion between one end of the connection line and the first transport line; and a movement connection portion that is provided in the other end of the connection line and is moved in each position capable of being connected to the respective second transport lines along with the rotation of the connection line and the electromagnet. Furthermore, in an upstream end portion of the second transport line, a second transport line opening and closing valve which opens and closes the second transport line may be provided, and the movement connection portion may have a connection line opening and closing valve that opens and closes the connection line, and a tubular expansion and contraction portion that is provided at a downstream side further than the connection line opening and closing valve, and is attached to and detached from the upstream end portion of the second transport line by being expanded and contracted in an advancement direction of the charged particle beam. The line switching step may have a first step of opening the vacuum in the expansion and contraction portion by closing the second transport line opening and closing valve of the second transport line connected to the movement connection portion and the connection line opening and closing valve; a second step of shortening the expansion and contraction portion to eliminate the connection between the expansion and contraction portion and the second transport line; a third step of rotating the connection line and the electromagnet to move the movement connection portion to another second transport line; a fourth step of expanding the expansion and contraction portion, connecting the same to the upstream end portion of another second transport line, and drawing the vacuum in the expansion and contraction portion; and a fifth step of opening the second transport line opening and closing valve of another second transport line and the connection line opening and closing valve.

According to the configuration, it is possible to switch the induction place of the charged particle beam, while maintaining the vacuum of the first transport line, the connection line, and the second transport line, by the closing and opening of the valve in the first to fifth steps, whereby the required volume of the vacuum drawing space can be minimized.

Furthermore, according to still another embodiment of the present invention, there is provided a method of attaching and detaching a transport line in which the movement connection portion of the line switching means in the charged particle beam irradiation apparatus is attached to and detached from the upstream end portion of any of the second transport line, the method includes a first step of opening the vacuum in the expansion and contraction portion by closing the second transport line opening and closing valve of the second transport line connected to the movement connection portion and the connection line opening and closing valve; a second step of shortening the expansion and contraction portion to eliminate the connection between the expansion and contraction portion and the second transport line; a third step of rotating the connection line and the electromagnet to move the movement connection portion to another second transport line; a fourth step of expanding the expansion and contraction portion, connecting the same to the upstream end portion of another second transport line, and drawing the vacuum in the expansion and contraction portion; and a fifth step of opening the second transport line opening and closing valve of another second transport line and the connection line opening and closing valve.

According to the method of attaching and detaching the transport line, it is possible to switch the induction place of the charged particle beam, while maintaining the vacuum of the first transport line, the connection line, and the second transport line, by the closing and opening of the valve in the first to fifth steps, whereby the volume of the required vacuum drawing space can be minimized.

According to the present invention, it is possible to provide a charged particle beam irradiation apparatus, a charged particle line irradiating method, and a method of attaching and detaching a transport line thereof capable of reducing the electromagnet number of the beam transport while reducing the site area of the installation place.

Hereinafter, a preferred embodiment of a charged particle beam irradiation apparatus of the present invention will be specifically described with reference to the drawings. In the present embodiment, a particle beam therapeutic apparatus as an example of the charged particle beam irradiation apparatus of the present invention will be described. In addition, if necessary, as shown in each drawing, an xyz coordinate system is set in which a z axis is a vertical axis and an xy plane is a horizontal plane, and in some cases, in the description of the positional relationship of each portion, x, y, and z are used for convenience. Furthermore, the terms "upstream" and "downstream" are used corresponding to the upstream and the downstream of the proton beam to be transported.

Figure 2:
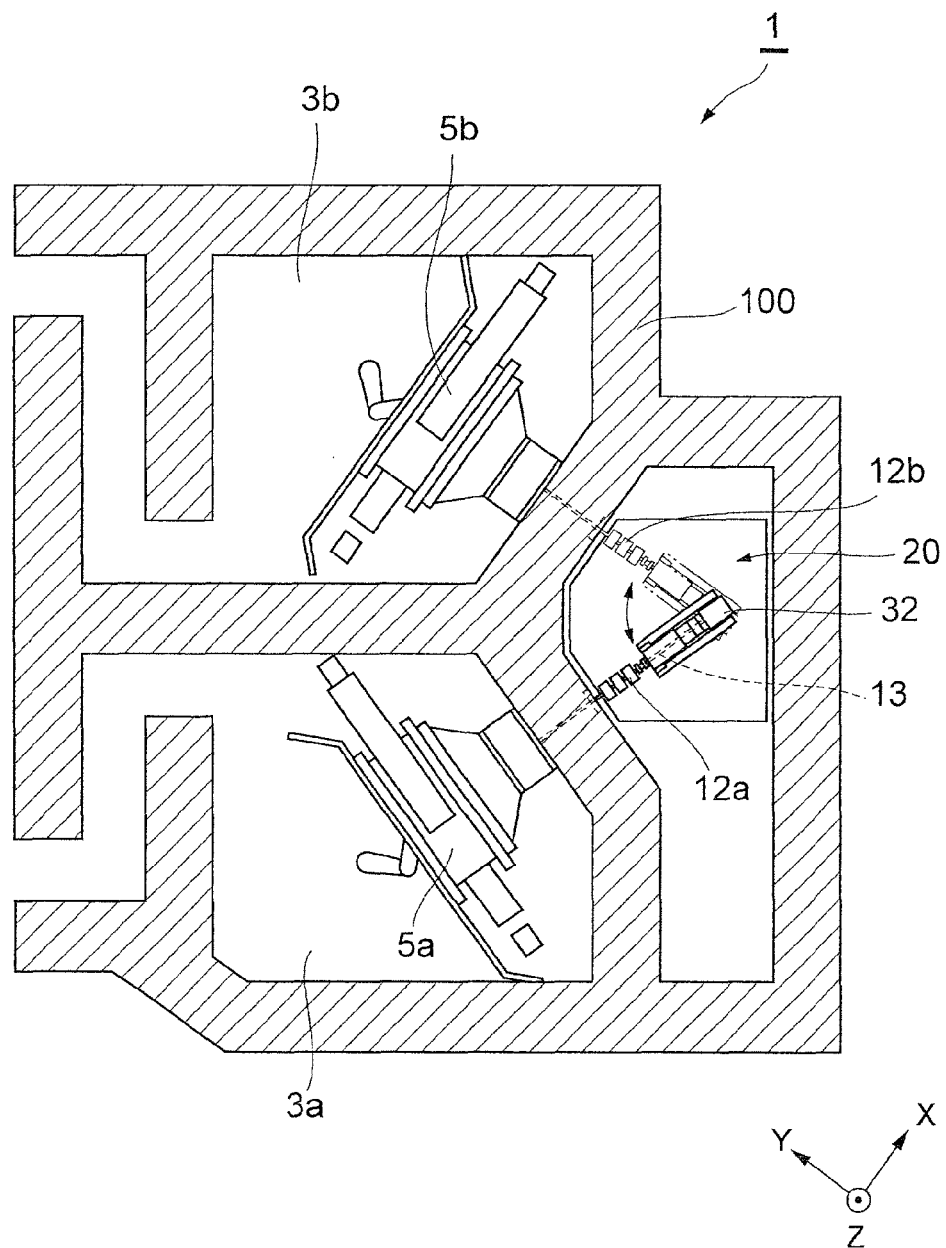
FIG. 2 is a plan view of the particle beam therapeutic apparatus of FIG. 1.

A particle beam therapeutic apparatus 1 shown in FIGS. 1 and 2 is applied to, for example, a cancer treatment, and is an apparatus that irradiates a tumor in a body of a patient (a radiation target) with the proton beam. As shown in the drawings, the particle beam therapeutic apparatus 1 includes two treatment rooms (irradiation chambers) 3a and 3b that are partitioned in a building 100, and two rotation gantries 5a and 5b that are installed in the treatment rooms 3a and 3b, respectively. The rotation gantries 5a and 5b are devices that irradiate the patient with the proton beam from an arbitrary direction. Two treatment rooms 3a and 3b are radially disposed in a horizontal plane around the connection portion 32 described later. Similarly, two rotation gantries 5a and 5b are also radially disposed in the horizontal plane around a connection portion 32 described later.

The particle beam therapeutic apparatus 1 includes an ion source 6 that creates hydrogen ions, an ion accelerator (accelerator) 7 that accelerates the hydrogen ion beam, removes the electron from the hydrogen ion, and outputs the proton beam, an energy adjustment portion 10 that is provided at an immediately downstream side of the ion accelerator 7, and a transport adjustment line 9 that transports the proton beam from the ion accelerator 7 to the rotation gantries 5a or 5b. The treatment rooms 3a and 3b are disposed in a predetermined floor (a second floor in the present embodiment) of the building 100, and meanwhile, the ion accelerator 7 is installed in another floor (a first floor in the present embodiment).

The energy adjustment portion 10 adjusts energy of the proton beam to be output from the ion accelerator 7. Since depths from a body surface of a patient to a tumor are different for each patient, when irradiating the patient with the proton beam, there is a need to adjust the reaching depth of the proton beam. The energy adjustment portion 10 adjusts the proton beam so as to suitably reach a tumor that is at a predetermined depth in a patient body, by adjusting energy of the proton beam.

The transport line 9 has a first transport line 11 that is situated at the upstream side of the proton beam and is connected to the energy adjustment portion 10, and second transport lines 12a and 12b that are situated at the downstream side of the proton beam and are connected to the rotation gantries 5a and 5b. Furthermore, the transport line 9 has a connection line 13 that is provided between the first transport line 11 and the second transport lines 12a and 12b.

The first transport line 11 forms a tubular shape that causes the proton beam to pass through a hollow portion, is extended horizontally from the ion accelerator 7, vertically stands up, and is extended from the first floor to the second floor of the building 100. The second transport lines 12a and 12b form a tubular shape that causes the proton beam to pass through the hollow portion, and are horizontally extended to the rotation gantries 5a and 5b in the second floor of the building 100, respectively. The second transport line 12a and the second transport line 12b have nearly the same length. The connection line 13 forms a tubular shape that causes the proton beam to pass through the hollow portion, and mediates between the first transport line 11 and any one of the second transport line 12a or 12b. The proton beam, which is input vertically upward from the first transport line 11 to the connection line 13, is bent by 90° due to the action of the deviation electromagnet 17 provided around the connection line 13, is converted to the horizontal direction, and is induced to the second transport lines 12a or 12b. The details of the connection line 13 will be described later.

A series of connected hollow portions of the first transport line 11, the connection line 13, and the second transport line 12a (12b) forms a vacuum, whereby a transport route of the proton beam is formed. Furthermore, around the first transport line 11, the connection line 13, and the second transport lines 12a and 12b, a deviation electromagnet 17 changing the direction of the proton beam or a shaping electromagnet 19 is suitably installed.

When the connection line 13 mediates the connection between the first transport line 11 and the second transport line 12a, the proton beam to be delivered from the ion accelerator 7 passes through the first transport line 11, the connection line 13, and the second transport line 12a and is sent to the rotation gantry 5a of the treatment room 3a in the connection line 13. That is, in this case, the particle beam irradiating method to a patient in the treatment room 3a is as below. Firstly, the hydrogen ion beam is accelerated by the ion accelerator 7 (a charged particle beam acceleration step). Next, the proton beam to be output from the ion accelerator 7 is transported vertically upward by the first transport line 11 (a first transport step), and the proton beam is induced to the second transport line 12a while horizontally deviation the advancement direction of the beam in the connection line 13. Moreover, the proton beam is transported to the rotation gantry 5a of the treatment room 3a by the second transport line 12a that is an induction place (a second transport step).

Similarly, when the connection line 13 mediates the connection between the first transport line 11 and the second transport line 12b, the proton beam to be delivered from the ion accelerator 7 passes through the first transport line 11, the connection line 13, and the second transport line 12b, and is sent to the rotation gantry 5b of the treatment room 3b. In this manner, by switching the connection state of the connection line 13 (a line switching step), the induction place of the proton beam can be switched between the second transport lines 12a and 12b, and thus the treatment room of a transport place of the proton beam can be switched.

Figure 3:
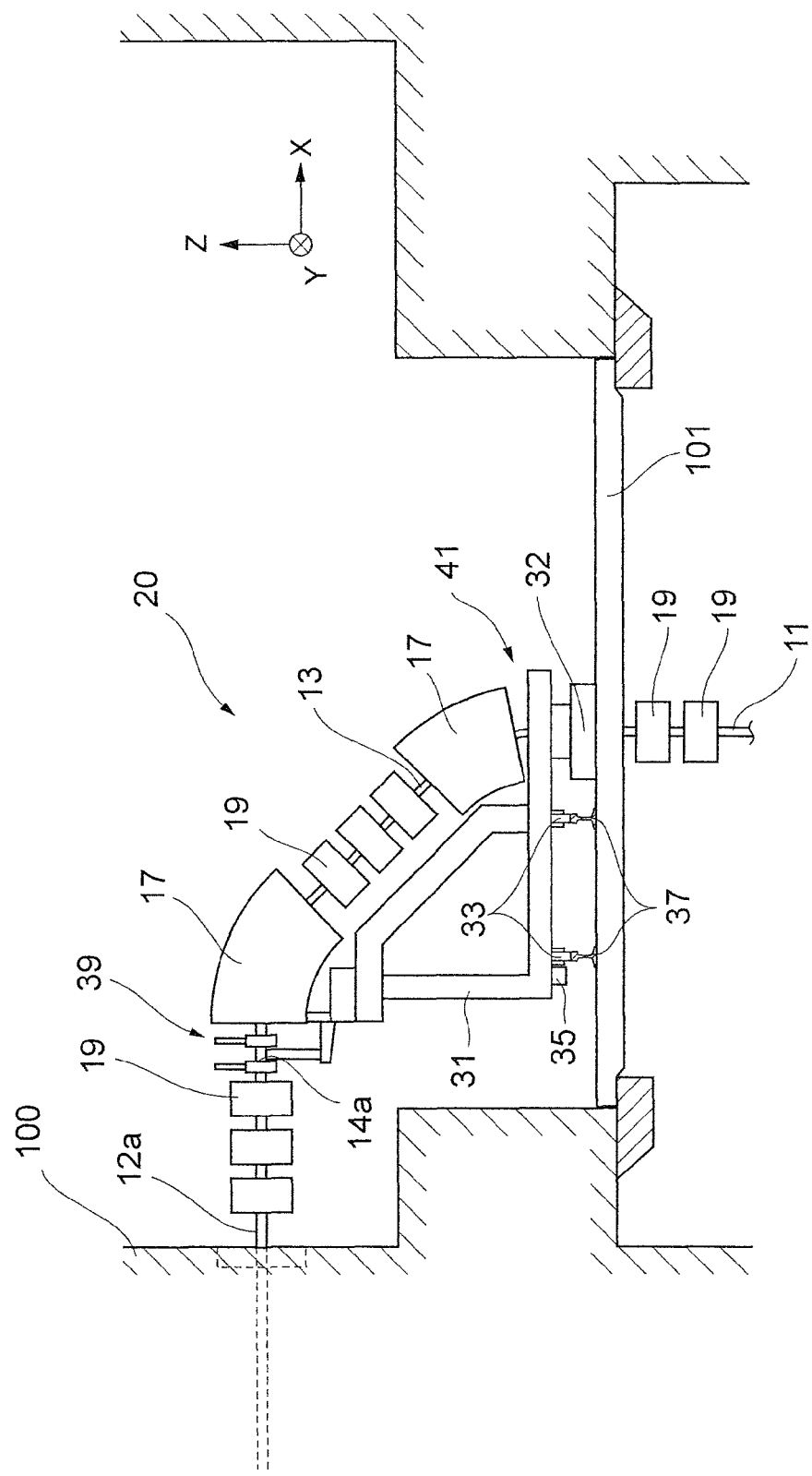
FIG. 3 is an enlarged side view of the vicinity of a switching device of the particle beam therapeutic apparatus of FIG. 1.
Figure 4:
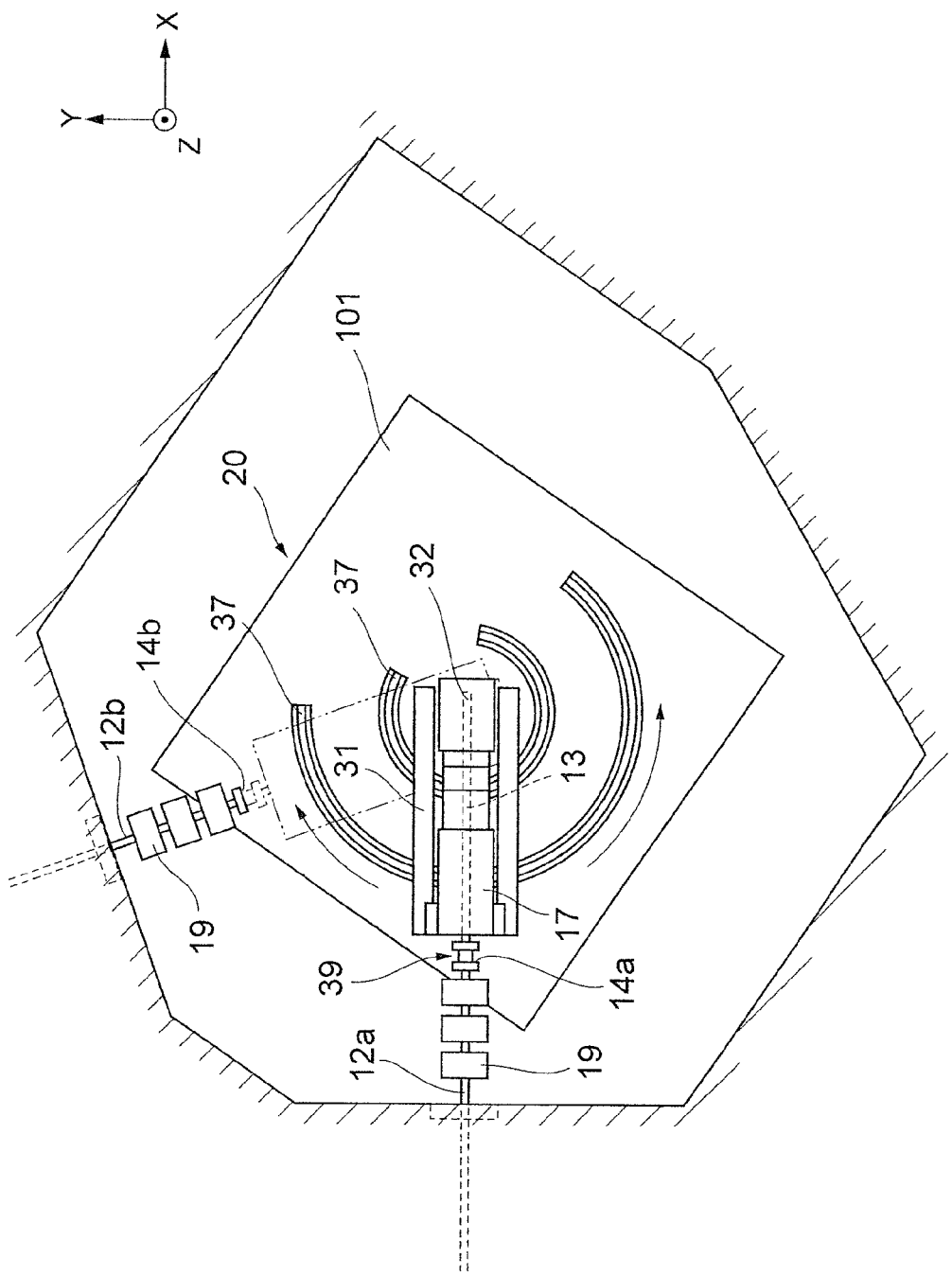
FIG. 4 is an enlarged plan view of the vicinity of the switching device of the particle beam therapeutic apparatus of FIG. 1.

Next, a switching device (line switching means) 20, which selectively switches the connection state of the connection line 13, will be further specifically described with reference to FIGS. 3 and 4. As shown in FIGS. 3 and 4, the switching device 20 is provided on the base 101 provided at the height of the second floor of the building 100. The switching device 20 is installed on a base 101 provided at the height of the second floor of the building 100. The switching device 20 includes the connection line 13, the deviation electromagnet 17 provided around the connection line 13, and the shaping electromagnet 19. Furthermore, the switching device 20 includes a turning table 31 on which the connection line 13, the deviation electromagnet 17, and the shaping electromagnet 19 are mounted and which can be rotated on the base 101.

One end of the connection line 13 is connected to the first transport line 11, and the connection line 13 can horizontally be rotated around a connection portion 32 between the connection line 13 and the first transport line 11. The other end of the connection line 13 is connected to an upstream end portion 14a of the second transport line 12a or an upstream end portion 14b of the second transport line 12b in an attachable or detachable manner. Hereinafter, a part of the other end of the connection line 13 capable of being connected to the respective upstream end portions 14a and 14b is referred to as a "movement connection portion", and is denoted by reference numeral "39". In addition, the respective upstream end portions 14a and 14b are disposed on the same circumference around the connection portion 32 when viewed in a plane.

The turning table 31 is supported so as to be horizontally rotatable around the connection portion 32 between the connection line 13 and the first transport line 11. On a lower surface of the turning table 31, two wheels 33 are mounted. Furthermore, on the base 101, two rails 37 forming a concentric arc shape when viewed in a plane are provided, and the wheels 33 are mounted on the rail 37, respectively. Furthermore, a motor 35 rotating the wheel 33 is attached to the turning table 31. When the wheel 33 is rotated by the driving of the motor 35, the wheel 33 is moved on the rail 37, whereby the turning table 31 is horizontally rotated around the connection portion 32. In addition, the motor 35 may be directly connected to the wheel 33, and may transmit the power of the motor 35 to the wheel 33 via a torque transmission mechanism (for example, a belt, a chain, a wire, a gear, a pinion, a circular rack or the like). The connection line 13 and the electromagnets 17 and 19 are also horizontally rotated along with the horizontal rotation of the turning table 31, and the movement connection portion 39 of the connection line 13 is moved between a position facing the upstream end portion 14a of the second transport line 12a and a position facing the upstream end portion 14b of the second transport line 12b. The movement connection portion 39 can be connected to the opposed upstream end portion 14a or 14b.

Figure 5:
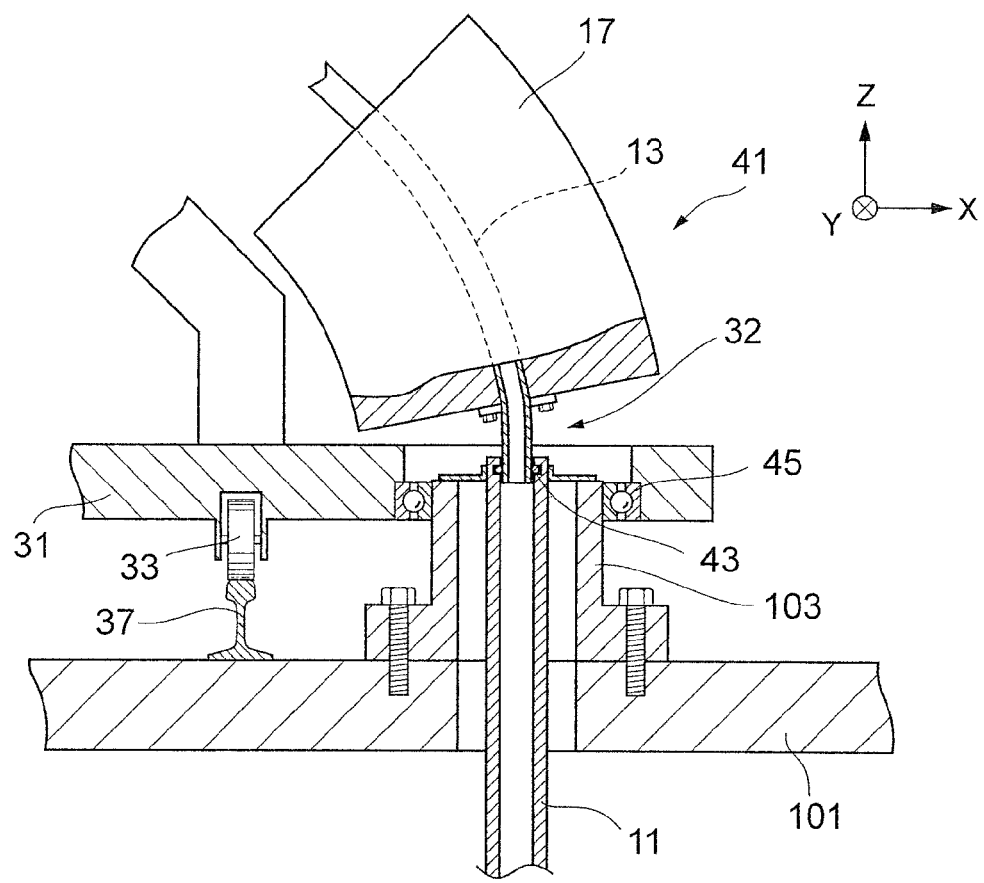
FIG. 5 is a cross-sectional view that shows a rotation support portion of the connection line of FIG. 3.

Next, a structure of a rotation support portion 41, which supports the connection line 13 in the vicinity of the connection portion 32 in a freely rotatable manner, will be described with reference to FIG. 5. The lower end of the connection line 13 is inserted into the upper end of the first transport line 11, whereby an outer peripheral surface of the connection line 13 comes into sliding contact with an inner peripheral surface of the first transport line 11. Since a gap between the connection line 13 and the first transport line 11 is sealed by a vacuum seal material 43, it is possible to form the vacuum in an internal beam transport path while enabling the connection line 13 to rotate with respect to the first transport line 11. In addition, it is possible to adopt a rubber O ring, an X ring, a magnetic fluid or the like as the vacuum seal material 43. On an upper surface of the base 101, a turning shaft portion 103 is mounted which inserts the first transport line 11 in a concentric position. Moreover, at the outside of the turning shaft portion 103, a turning table 31 is mounted via a bearing 45 around the connection portion 32. A rotation mechanism is realized by the structure as mentioned above, and the turning table 31 can be horizontally rotated around the connection portion 32.

Figure 6:
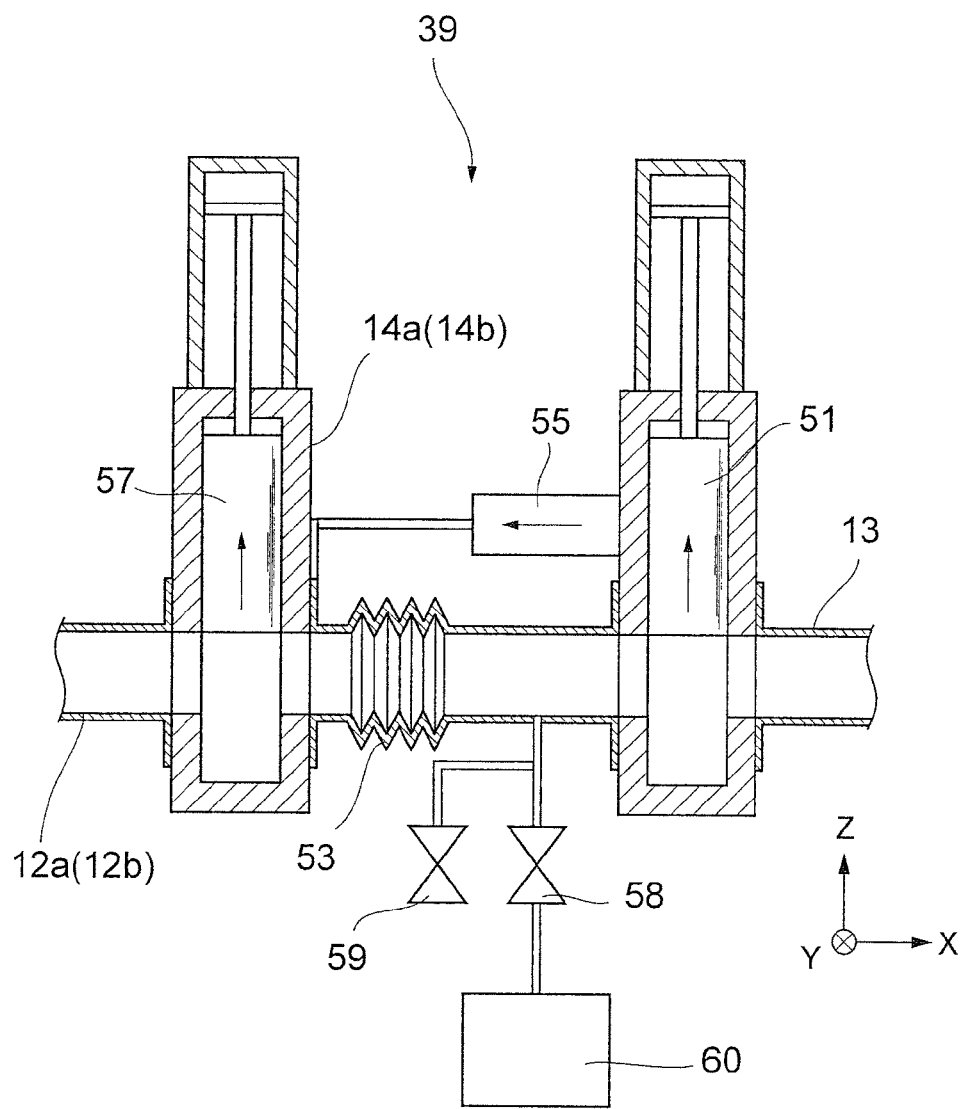
FIG. 6 is a cross-sectional view that shows a stretched state of a movement connection portion of a connection line of FIG. 3.
Figure 7:
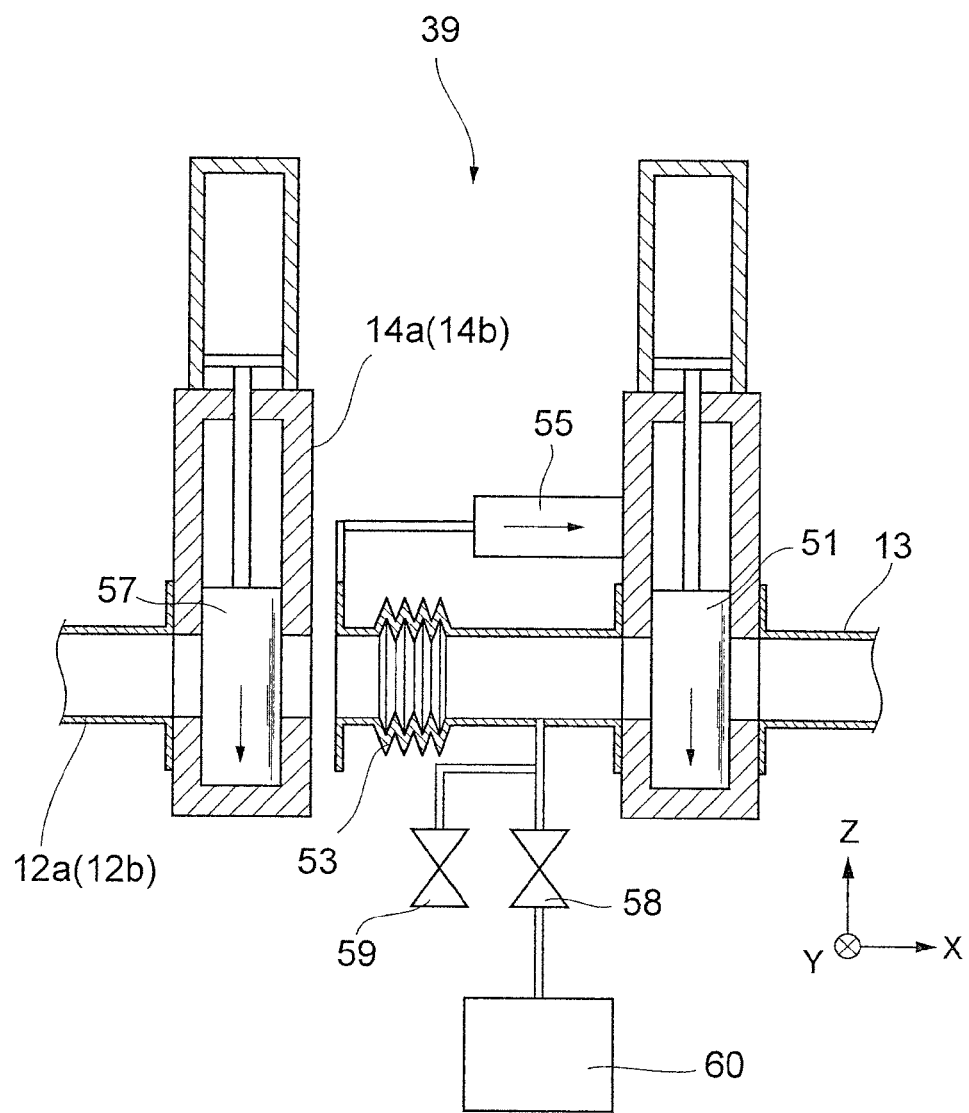
FIG. 7 is a cross-sectional view that shows a shortened state of the movement connection portion of FIG. 6.

Next, a structure of the vicinity of the movement connection portion 39 of the connection line 13 will be described with reference to FIGS. 6 and 7. As shown in FIGS. 6 and 7, in the movement connection portion 39, a connection line opening and closing valve 51 is provided which opens and closes the connection line 13. At the downstream side of the connection line opening and closing valve 51, a bellows portion 53 is provided which is expanded and contracted in the advancement direction of the beam. The bellows portion 53 can be attached to or detached from the upstream end portion 14a of the second transport line 12a by the expansion and the contraction. An air cylinder 55 is provided at the side of the bellows portion 53, and the expansion and the contraction of the bellows portion 53 is realized by the driving of the air cylinder 55. Furthermore, a hydraulic cylinder may be used instead of the air cylinder 55.

Furthermore, in the upstream end portion 14a of the second transport line 12a, a second transport line opening and closing valve 57 which opens and closes the second transport line 12a is also mounted. Further, a vacuum pump 60 for evacuating the inside of the bellows portion 53 and a vacuum seal valve 58 are provided in the movement connection portion 39. Furthermore, in the movement connection portion 39, an atmosphere opening valve 59 is also provided which opens the inner portion of the bellows portion 53 to the atmosphere.

Based on the configuration of such a switching device 20, as shown in FIG. 6, in the state in which the opening and closing valves 51 and 57 are opened and the bellows portion 53 comes into close contact with the upstream end portion 14a, the connection line 13 and the second transport line 12a are connected to each other, whereby the transport route of the proton beam is formed. Furthermore, as shown in FIG. 7, in the state in which the opening valves 51 and 57 are closed and the bellows portion 53 is separated from the upstream end portion 14a, the movement connection portion 39 can be freely moved by the rotation of the turning table 31 mentioned above. In addition, in FIGS. 6 and 7, the connection structure between the connection line 13 and the second transport line 12a is described. However, since the connection structure between the connection line 13 and the second transport line 12b is exactly the same, the repeated description will be omitted.

Next, a method of attaching and detaching the connection line 13 to the second transport lines 12a and 12b will be described with reference to FIGS. 6 and 7.

When the movement connection portion 39 is currently connected to the second transport line 12a, the opening and closing valve 57 of the second transport line 12a and the opening and closing valve 51 of the movement connection portion 39 are closed. Moreover, the atmosphere opening valve 59 is opened to open the vacuum in the bellows 53 (a first step). Moreover, the air cylinder 55 is driven to shorten the bellows portion 53 and is separated from the upstream end portion 14a (a second step). In this manner, like FIG. 7, the state is obtained in which the connection between the connection line 13 and the second transport line 12 is released. Next, by rotating the turning table 31 (see FIG. 3) by the driving of the motor 35, the movement connection portion 39 is moved to a position facing the upstream end portion 14b of the second transport line 12a (a third step). Next, the air cylinder 55 is driven to stretch the bellows portion 53 and is brought into close contact with the upstream end portion 14b. Moreover, by driving the vacuum pump 60 to open the vacuum sealing valve 58, the inner portion of the bellows portion 53 is subjected to the vacuum drawing (a fourth step). Next, by opening the opening and closing valve 57 of the second transport line 12b and the opening and closing valve 51 of the movement connection portion 39 (a fifth step), the state of FIG. 6 is obtained, whereby the proton beam transport route for sending the proton beam to the treatment room 3b is formed. In addition, when the turning table 31 is rotated or when the bellows portion 53 is expanded or contracted, an accurate rotation position and an expansion and contraction position are realized by the use of a position sensor (not shown). Furthermore, if a latch mechanism is adopted, it is possible to omit position detection by the position sensor.

By such a sequence, it is possible to switch the connection place of the connection line 13 between the second transport lines 12a and 12b. Furthermore, according to the attaching or detaching method, it is possible to switch the induction place of the proton beam while maintaining the vacuum of the first transport line 11, the connection line 13, and the second transport lines 12a and 12b. Thus, since only the inner portion of the bellows portion 53 requires the vacuum drawing, the volume of the vacuum drawing space can be minimized. In addition, since the beam transport route in the bellows portion 53 has a short distance, the vacuum drawing in the bellows portion 53 may be omitted.

According to the particle beam therapeutic apparatus 1 mentioned above, by horizontally rotating the connection line 13 and the electromagnets 17 and 19, it is possible to switch the second transport lines 12a and 12b of the induction place of the proton beam, and thus it is possible to switch the treatment rooms 3a and 3b to which the proton beam is sent. In this manner, since a type of rotating the connection line 13 and switching the connection place is adopted as a type of switching the transport place of the proton beam, it is possible to reduce the number of the required electromagnet compared to the type of switching the operating states (On/Off) of the electromagnet like the related art. Furthermore, since a plurality of treatment rooms 3a and 3b are radially disposed around the rotation support portion 41 of the connection line 13, an unnecessary installation space is reduced, whereby it is possible to reduce the site area of the installation location of the particle beam therapeutic apparatus 1.

Furthermore, in the particle beam therapeutic apparatus 1, the treatment rooms 3a and 3b and the ion accelerator 7 are provided in different floors of the building, and the first transport line 11 is extended from a floor provided with the ion accelerator 7 to a floor provided with the treatment rooms 3a and 3b. According to the configuration, it is possible to reduce a projection area of the first transport line 11 when viewed from above, whereby it is possible to reduce the installation area as a whole of the particle beam therapeutic apparatus 1. Furthermore, as shown in FIG. 1, the ion accelerator 7 can be provided immediately below the rotation gantries 5a and 5b, whereby it is possible to reduce the installation area of the particle beam therapeutic apparatus 1 when viewed from above.

Figure 8:
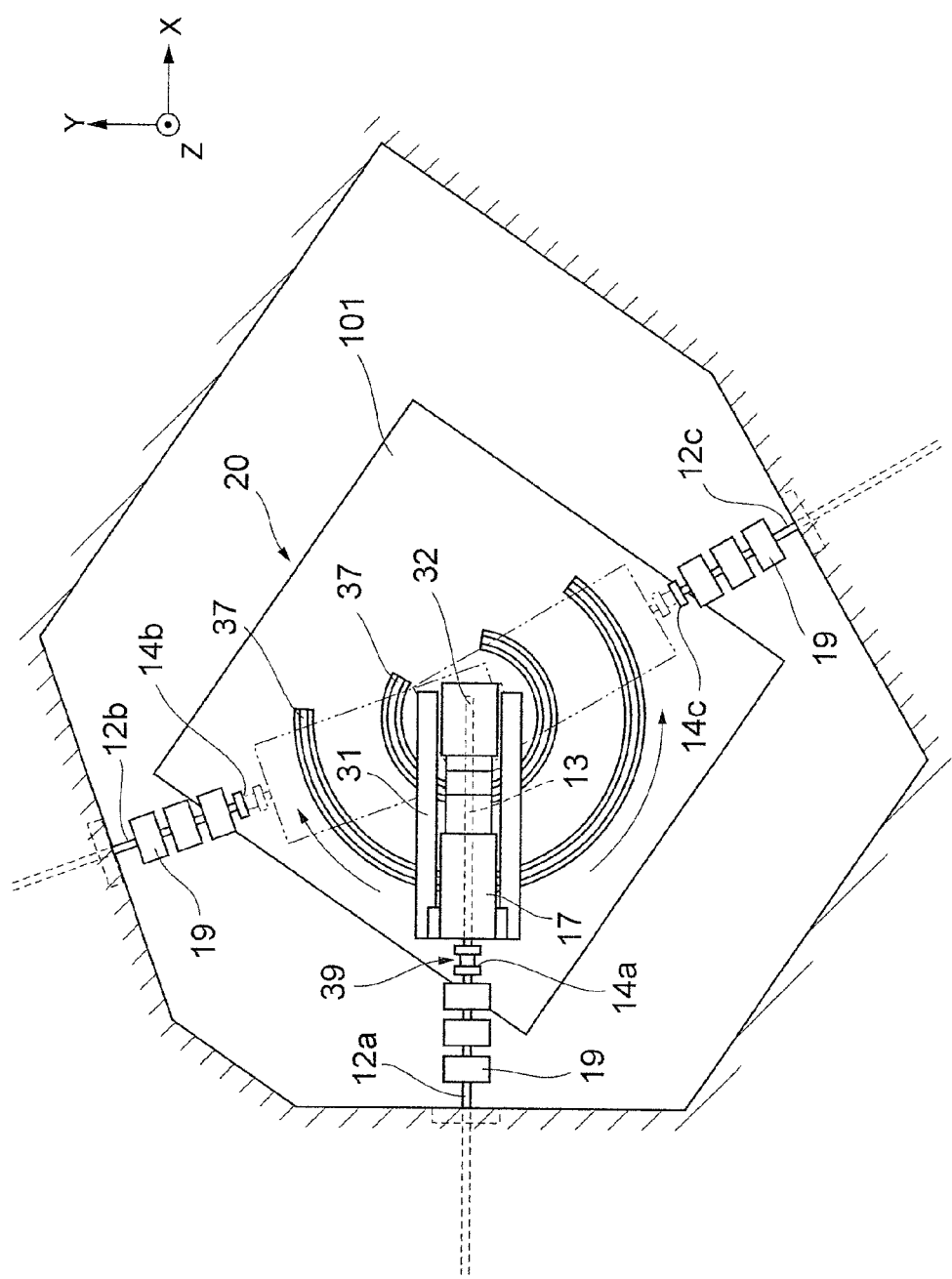
FIG. 8 is a plan view that shows a state in which a second transport line is established to a greater extent in the particle beam therapeutic apparatus of FIG. 1.

Furthermore, in the particle beam therapeutic apparatus 1, the first transport line 11 is vertically extended, and meanwhile, the second transport lines 12a and 12b are horizontally extended. Thus, the connection line 13 needs to bias the proton beam by 90°. Due to this structure, the configuration mentioned above is suitably applied in which connection ports (the upstream end portions 14a and 14b) of the second transport lines 12a and 12b are disposed at the same distance from the center (the connection portion 32) of the horizontal rotation of the connection line 13. Furthermore, according to the configuration, when establishing more treatment rooms, for example, as shown in FIG. 8, a second transport line 12c which transports the proton beam to a new treatment room may be additionally established, and an upstream end portion 14c may be disposed at the same distance from the connection portion 32. Thus, there is no need to change the structure of the connection line 13, and it is also relatively easy to establish additional treatment rooms.

Certain embodiments of the present invention are not limited to the embodiment mentioned above. For example, the position of the ion accelerator is not limited to a position overlapping with the treatment room when viewed from above, but the ion accelerator may be disposed obliquely below the treatment room. Furthermore, the vertical position relationship between the ion accelerator and the treatment room is also not limited to the embodiment, but the ion accelerator may be provided in the floor of the upper level, and the treatment room bay be provided in the floor of the lower level. Furthermore, the ion accelerator and the treatment room may be provided in the same level.

Furthermore, the accelerator may be a synchrotron, a synchrocyclotron or the like, without being limited to the ion accelerator. Furthermore, without providing the rotation gantry in the treatment room (the irradiation chamber), the treatment room may be a rotation irradiation type using the rotation arm, or may be a fixed irradiation type instead of the rotation irradiation type. Furthermore, the charged particle is not limited to hydrogen but may be carbon or the like. Furthermore, a configuration may be adopted in which an ion source is provided in the ion accelerator and the hydrogen ion is created in the ion accelerator, without being limited to a configuration in which the hydrogen ion is created by the ion source provided outside the ion accelerator and the hydrogen ion is supplied to the ion accelerator.

Furthermore, a structure as below may be adopted instead of the bellows portion (the expansion and contraction portion) 53. That is, in a structure in which a small-diameter barrel is concentrically inserted into the inside of a large-diameter barrel, a structure is considered in which the large-diameter barrel (or the small-diameter barrel) is moved back and forth in a barrel axis direction. In this case, as the mechanism that moves the large-diameter barrel (or the small-diameter barrel) back and forth, an air cylinder, an electric cylinder, a hydraulic cylinder, a mechanism in which a ball screw and a motor are combined with each other or the like is considered. Furthermore, as vacuum seal means between the large-diameter barrel and the small-diameter barrel, an O ring or an X ring can be used.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation apparatus that includes a plurality of irradiation chambers, and irradiates irradiation targets in the irradiation chambers with a charged particle beam, the apparatus comprising:
    an accelerator that accelerates the charged particle beam;
    a first transport line that transports the charged particle beam which is delivered from the accelerator;
    a plurality of second transport lines that are provided for each of a plurality of irradiation chambers and further transport the charged particle beam to be transported by the first transport line to the respective irradiation chambers; and
    a line switching unit that is provided between the first transport line and the plurality of second transport lines, induces the charged particle beam from the first transport line to any of the plurality of second transport lines, and can selectively switch the second transport line of an induction place,
    wherein the plurality of irradiation chambers is radially disposed around the line switching unit,
    the line switching unit includes an electromagnet that induces the charged particle beam, and a rotating mechanism that rotates the electromagnet, and
    the plurality of second transport lines of the induction place are switched by rotating the electromagnet; and
    wherein the line switching unit includes:
        a tubular connection line that is provided with the electromagnet, mediates the connection between the first transport line of a tubular shape and one of the plurality of second transport lines of a tubular shape, and causes the charged particle beam to pass therethrough;
        a rotation support portion that rotatably supports the connection line and the electromagnet around a connection portion between one end of the connection line and the first transport line; and
        a movement connection portion that is provided in another end of the connection line and is moved in each position capable of being connected to the respective second transport lines along with rotation of the connection line and the electromagnet, and
    wherein, in an upstream end portion of the second transport line, a second transport line opening and closing valve which opens and closes the second transport line is provided, and the movement connection portion includes:
        a connection line opening and closing valve that opens and closes the connection line; and
        a tubular expansion and contraction portion that is provided at a downstream side further than the connection line opening and closing valve, and is attached to and detached from the upstream end portion of the second transport line by being expanded and contracted in an advancement direction of the charged particle beam.

2. The charged particle beam irradiation apparatus according to claim 1,
    wherein a plurality of irradiation chambers and the accelerator are provided in different floors of a building, and
    the first transport line is extended from a floor provided with the accelerator to a floor provided with the irradiation chamber.

3. A charged particle beam irradiating method of irradiating an irradiation target in a plurality of irradiation chambers with a charged particle beam, the method comprising:
    a charged particle beam acceleration step of accelerating the charged particle beam by an accelerator,
    a first transport step of transporting the charged particle beam accelerated at the charged particle beam acceleration step by a first transport line;
    a second transport step of transporting the charged particle beam to be transported at the first transport step to the plurality of irradiation chambers, by any of second transport lines provided for each of the plurality of irradiation chambers; and
    a line switching step of selectively switching the second transport line of an induction place by a line switching unit that is provided between the first transport line and the second transport lines and induces the charged particle beam from the first transport line to any one of second transport lines,
    wherein the plurality of irradiation chambers is radially disposed around the line switching unit,
    the line switching unit includes an electromagnet that induces the charged particle beam, and a rotating mechanism that rotates the electromagnet, and
    at the line switching step, the second transport lines of the induction place are switched by rotating the electromagnet,
    wherein the line switching unit includes
    a tubular connection line that is provided with an electromagnet, mediates a connection between the first transport line of a tubular shape and the second transport line of a tubular shape, and causes the charged particle beam to pass therethrough;
    a rotation support portion that rotatably supports the tubular connection line and the electromagnet around a connection portion between one end of the tubular connection line and the first transport line; and
    a movement connection portion that is provided in another end of the tubular connection line and is moved in each position capable of being connected to the respective second transport lines along with a rotation of the tubular connection line and the electromagnet,
    in an upstream end portion of the second transport line, a second transport line opening and closing valve is provided which opens and closes the second transport lines,
    the movement connection portion includes
    a connection line opening and closing valve that opens and closes the tubular connection line; and
    a tubular expansion and contraction portion that is provided at a downstream side further than the connection line opening and closing valve, and is attached to and detached from the upstream end portion of the second transport line by being expanded and contracted in an advancement direction of the charged particle beam, and
    the line switching step includes
    a first step of opening a vacuum in the tubular expansion and contraction portion by closing the second transport line opening and closing valve of the second transport line to be connected to the movement connection portion and the connection line opening and closing valve;

a second step of shortening the tubular expansion and contraction portion to eliminate a connection between the tubular expansion and contraction portion and the second transport line;

a third step of rotating the connection line and the electromagnet to move the movement connection portion to another second transport line;

a fourth step of expanding the tubular expansion and contraction portion, connecting the same to the upstream end portion of another second transport line, and drawing the vacuum in the tubular expansion and contraction portion; and a fifth step of opening the second transport line opening and closing valve of another second transport line and the connection line opening and closing valve.

* * * * *